US00PP33465P2

(12) United States Plant Patent
Kientzler

(10) Patent No.: US PP33,465 P2
(45) Date of Patent: Sep. 7, 2021

(54) **NEW GUINEA *IMPATIENS* PLANT NAMED 'KITORITO'**

(50) Latin Name: *Impatiens hawkeri*
Varietal Denomination: Kitorito

(71) Applicant: Ludwig Kientzler, Gensingen (DE)

(72) Inventor: Ludwig Kientzler, Gensingen (DE)

(73) Assignee: Innovaplant Zierpflanzen GmbH & Co. KG, Gensingen (DE)

( * ) Notice: Subject to any disclaimer, the term of this patent is extended or adjusted under 35 U.S.C. 154(b) by 0 days.

(21) Appl. No.: 17/111,300

(22) Filed: Dec. 3, 2020

(51) Int. Cl.
*A01H 5/02* (2018.01)
*A01H 6/16* (2018.01)

(52) U.S. Cl.
USPC ..... Plt./318.3
CPC ..... *A01H 6/165* (2018.05)

(58) Field of Classification Search
USPC ..... Plt./318.3, 318.1
CPC ..... A01H 6/165; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of New Guinea Impatiens plant named 'Kitorito', characterized by its compact, upright to broadly spreading and mounded plant habit; freely branching habit; dense and bushy growth habit; dark green-colored leaves; numerous reddish orange-colored flowers with central white-colored star pattern; and flowers positioned above and beyond the foliar plane.

2 Drawing Sheets

Botanical designation: *Impatiens hawkeri.*
Cultivar denomination: 'KITORITO'.

STATEMENT REGARDING PRIOR DISCLOSURES BY INVENTOR/APPLICANT & ASSIGNEE

An European Community Plant Breeder's Rights application for the instant plant was filed by the Assignee, Innovaplant Zierpflanzen GmbH & Co. KG of Gensingen, Germany on Jul. 28, 2020, application number 2020/1787. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of New Guinea Impatiens plant, botanically known as *Impatiens hawkeri*, and hereinafter referred to by the name 'Kitorito'.

The new *Impatiens* plant is a product of a planned breeding program conducted by the Inventor in Gensingen, Germany. The objective of the breeding program was to develop new compact and freely branching *Impatiens* plants with numerous flowers and attractive leaf and flower colors.

The new *Impatiens* plant originated from a cross-pollination made by the Inventor in November, 2016 of *Impatiens hawkeri*'Kimustique', not patented, as the female, or seed, parent with a proprietary selection of the *Impatiens hawkeri* identified as code number 171/2014, not patented, as the male, or pollen, parent. The new *Impatiens* plant was discovered and selected by the Inventor as a flowering plant within the progeny of the stated cross-pollination in a controlled greenhouse environment in Gensingen, Germany in April, 2017.

Asexual reproduction of the new *Impatiens* plant by terminal cuttings propagated in a controlled greenhouse environment in Gensingen, Germany since June, 2017 has shown that the unique features of this new *Impatiens* plant are stable and reproduced true to type in successive generations of asexual reproduction.

SUMMARY OF THE INVENTION

Plants of the new *Impatiens* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Kitorito'. These characteristics in combination distinguish 'Kitorito' as a new and distinct *Impatiens* plant:

1. Compact, upright to broadly spreading and mounded plant habit.
2. Freely branching habit; dense and bushy growth habit.
3. Dark green-colored leaves.
4. Numerous reddish orange-colored flowers with central white-colored star pattern.
5. Flowers positioned above and beyond the foliar plane.

Plants of the new *Impatiens* differ primarily from plants of the female parent, 'Kimustique', in flower color as plants of the new *Impatiens* have reddish orange-colored flowers with a central white-colored star pattern whereas plants of 'Kimustique' are reddish salmon in color.

Plants of the new *Impatiens* differ primarily from plants of the male parent selection in plant habit as plants of the new *Impatiens* are more uniform than plants of the male parent selection.

Plants of the new *Impatiens* can be compared to plants of *Impatiens hawkeri* 'DANHAR305', disclosed in U.S. Plant Pat. No. 21,306. In side-by-side comparisons, plants of the new *Impatiens* differ primarily from plants of 'DANHAR305', in flower color as plants of the new *Impatiens* have reddish orange-colored flowers with a central white-colored star pattern whereas plants of 'DANHAR305' are orange in color with white-colored centers.

BRIEF DESCRIPTION OF THE PHOTOGRAPHS

The accompanying photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph on the first sheet is a side perspective view of a typical flowering plant of 'Kitorito' grown in a container.

The photograph on the second sheet are close-up views of the upper surfaces (top of sheet) and lower surfaces (bottom of sheet) of typical flowers and leaves of 'Kitorito'.

DETAILED BOTANICAL DESCRIPTION

The aforementioned photographs and following observations and measurements describe plants grown in Gensingen, Germany during the summer in 12-cm containers in a glass-covered greenhouse and under cultural practices typical of commercial New Guinea Impatiens production. During the production of the plants, day temperatures ranged from 18° C. to 25° C. and night temperatures ranged from 20° to 22° C. Plants were twelve weeks old when the photographs and detailed description were taken. In the following description, color references are made to The Royal Horticultural Society Colour Chart, 2015 Edition, except where general terms of ordinary dictionary significance are used.

Botanical classification: *Impatiens hawkeri* 'Kitorito'.

Parentage:

- *Female, or seed, parent.*—*Impatiens hawkeri* 'Kimustique', not patented.
- *Male, or pollen parent.*—Proprietary selection of *Impatiens hawkeri* identified as code number 171/2014, not patented.

Propagation:

- *Type.*—By terminal vegetative cuttings.
- *Time to initiate roots, summer.*—About eight to ten days at temperatures about 20° C. to 35° C.
- *Time to initiate roots, winter.*—About ten to twelve days at temperatures about 20° C. to 25° C.
- *Time to produce a rooted young plant, summer.*—About two to three weeks at temperatures about 20° C. to 35° C.
- *Time to produce a rooted young plant, winter.*—About three to four weeks at temperatures about 20° C. to 25° C.
- *Root description.*—Fibrous, medium in thickness; typically white in color, actual color of the roots is dependent on substrate composition, water quality, fertilizers, substrate temperature and physiological age of roots.
- *Rooting habit.*—Moderately freely branching; medium density.

Plant description:

- *Plant and growth habit.*—Compact, upright to broadly spreading and mounded plant habit; moderately vigorous and moderate growth rate.
- *Branching habit.*—Freely branching habit; about five primary lateral branches developing at the base each with about 2.5 secondary branches; dense and bushy growth habit; pinching, that is, removal of the terminal apices, is typically not required.
- *Plant height, soil level to top of foliar plane.*—About 13.1 cm.
- *Plant height, soil level to top of floral plane.*—About 17.1 cm.
- *Plant diameter or spread.*—About 32.6 cm.
- *Lateral branches.*—Length: About 5.4 cm. Diameter: About 5.5 mm. Internode length: About 2.8 cm. Strength: Moderately strong. Aspect: About 40° to 60° from vertical. Texture and luster: Smooth, glabrous; glossy. Color, developing: Close to between 183A and187A. Color, developed: Upper surface, close to 187B; lower surface, close to 178B; at the internodes, close to 187B; oldest stems, close to 178A to 178B.

Leaf description:

- *Arrangement.*—Opposite or in whorls, single.
- *Length.*—About 9.9 cm.
- *Width.*—About 3.5 cm.
- *Shape.*—Narrowly elliptic to narrowly ovate.
- *Apex.*—Long apiculate.
- *Base.*—Long attenuate.
- *Margin.*—Serrulate with ciliation.
- *Texture and luster, upper surface.*—Smooth, glabrous; slightly glossy.
- *Texture and luster, lower surface.*—Smooth, glabrous; very slightly glossy.
- *Venation pattern.*—Pinnate.
- *Color.*—Developing leaves, upper surface: Close to NN137A. Developing leaves, lower surface: Close to 138B. Fully expanded leaves, upper surface: Close to NN137A tinged with close to 147A; venation, close to 180A to 180B. Fully expanded leaves, lower surface: Close to 147B; venation, close to 176B.
- *Petioles.*—Length: About 2.7 cm. Diameter: About 3 mm by 4 mm. Strength: Moderately strong; flexible. Texture and luster, upper surface: Smooth, glabrous; glossy. Texture and luster, lower surface: Smooth, glabrous; moderately glossy. Color, upper surface: Close to 181A. Color, lower surface: Close to 182B.

Flower description:

- *Flower type and flowering habit.*—Single axillary flowers; freely flowering habit with usually about 93 flower buds and flowers developing per plant; flowers positioned above and beyond the foliar plane and typically face upright to slightly outwardly.
- *Flower longevity.*—Flowers last about ten days under greenhouse conditions; petals self-cleaning, gynoecium persistent.
- *Fragrance.*—None detected.

*Natural flowering season.*—Year-round under greenhouse conditions; in the garden, flowering from spring until fall in California; plants begin flowering about 60 to 70 days after planting young plants.

*Flower diameter.*—About 6.5 cm by 7.3 cm.

*Flower depth.*—About 2.3 cm; with spur, close to 4.8 cm.

*Flower buds.*—Length: About 2 cm. Diameter: About 1.3 cm by 1.4 cm. Shape: Ovoid; spurred. Texture and luster: Smooth, glabrous; slightly glossy. Color: Petals, close to 32A; 48D and N34C with apices, close to 146B to 146C; sepals, close to between 152B and 199A; spur, close to 48B and 53B.

*Petals.*—Quantity and arrangement: Five petals arranged in a single whorl; one banner petal, two lateral petals and two lower petals. Length, banner petal: About 3.5 cm. Length, lateral petals: About 3.2 cm. Length, lower petals: About 3.8 cm. Width, banner petal: About 5.2 cm. Width, lateral petals: About 3.2 cm. Width, lower petals: About 3.7 cm. Shape, banner petal: Reniform. Shape, lateral and lower petals: Obcordate. Apex, all petals: Broadly emarginate. Base, banner petal: Truncate. Base, lateral and lower petals: Attenuate. Margin, all petals: Entire; moderately and coarsely undulate. Texture and luster, all petals, upper surface: Smooth, glabrous; velvety; matte. Texture and luster, all petals, lower surface: Smooth, glabrous; slightly velvety; matte. Color, banner petal: When opening, upper surface: Close to N30B and 32A; towards the base, close to 48D. When opening, lower surface: Close to 32A and 35A; keel, close to 197B; central blotch surrounding keel, close to 50A. Fully opened, upper surface: Close to between N30B and 33A; towards the base, close to 69A to 69B; venation, similar to lamina colors. Fully opened, lower surface: Close to 32A; keel, close to 197B; central blotch surrounding keel, close to 52B; venation, similar to lamina colors. Color, lateral petals: When opening, upper surface: Close to N30B and 32A; towards the base, close to 58C and 69B to 69C. When opening, lower surface: Close to 39B; towards the base, close to 58C and 68C. Fully opened, upper surface: Close to N30B; towards the base, close to 58B to 58C and 69D; venation, similar to lamina colors. Fully opened, lower surface: Close to 34C and 35A; towards the base, close to 59D; venation, similar to lamina colors. Color, lower petals: When opening, upper surface: Close to N30B and 32A; towards the base, close to 62B to 62C and 69B to 69C. When opening, lower surface: Close to 35A; towards the base, close to 58C and 68C. Fully opened, upper surface: Close to N30B; towards the base, close to NN155C; at the base, close to 59D; venation, similar to lamina colors. Fully opened, lower surface: Close to 35B; towards the base, close to 58B and 69C; venation, similar to lamina colors.

*Sepals.*—Quantity and arrangement: Three arranged in a single whorl; one dorsal sepal modified into an elongated spur and two lateral sepals. Length, dorsal sepal (excluding spur): About 1.8 cm. Length, lateral sepals: About 1.3 cm. Width, dorsal sepal: About 1.3 cm. Width, lateral sepals: About 7 mm. Shape, dorsal sepal: Broadly ovate. Shape, lateral sepals: Ovate. Apex, dorsal sepal: Acute. Apex, lateral sepals: Apiculate. Base, all sepals: Cuneate. Margin: Entire. Texture and luster, upper surface, all sepals: Smooth, glabrous; matte. Texture and luster, lower surface, all sepals: Smooth, glabrous; slightly glossy. Color, dorsal sepal: When opening, upper surface: Close to 69B; towards the apex and margins, close to 52A. When opening, lower surface: Close to 69B; towards the base, close to 50C; towards the margins, close to 52A; central band and towards the apex, close to 180B. Fully opened, upper surface: Close to 69B; towards the apex and margins, close to 50A to 50B. Fully opened, lower surface: Close to 69B; towards the base, close to 54C; towards the margins, central band and towards the apex, close to 52B. Color, lateral sepals: When opening, upper and lower surfaces: Close to 182A to 182B; towards the apex and margins, tinged with close to 146D. Fully opened, upper surface: Close to 51A to 51B; towards the apex and margins, tinged with close to 145C. Fully opened, lower surface: Close to 182A; towards the apex and margins, tinged with close to 147D. Spur length: About 4.6 cm. Spur diameter: At flower, about 1.5 mm; at apex, less than 1 mm. Spur texture and luster: Smooth, glabrous; glossy. Spur color: Close to N34A; towards the apex, close to 46A; towards the base, close to 51B.

*Peduncles.*—Length: About 7 cm. Diameter: About 1.75 mm. Angle: About 45° from vertical. Strength: Relatively weak. Texture and luster: Smooth, glabrous; glossy. Color, upper surface: Close to 183A. Color, lower surface: Close to 183B.

*Reproductive organs.*—Stamens: Quantity: Four. Filament length: About 4.5 mm. Filament color: Close to 43C. Anther size: About 1 mm by 3 mm. Anther shape: Oblong. Anther color: Close to 16B. Pollen amount: Moderate. Pollen color: Close to 11D. Pistils: Quantity per flower: One. Pistil length: About 1 mm. Style length: About 0.5 mm. Style color: Close to 157A. Stigma diameter: About 0.8 mm. Stigma shape: Round, flattened. Stigma color: Close to 157A. Ovary color: Close to 144B.

*Seeds and fruit.*—To date, seed nor fruit development has not been observed on plants of the new *Impatiens*.

Pathogen & pest resistance: To date, plants of the new *Impatiens* have not been observed to be resistant to pathogens and pests common to New Guinea Impatiens plants.

Temperature tolerance: Plants of the new *Impatiens* have been observed to tolerate temperatures from about 5° C. to about 40° C. and to be suitable for USDA Hardiness Zones 10 to 13.

It is claimed:

1. A new and distinct New Guinea Impatiens plant named 'Kitorito' as illustrated and described.

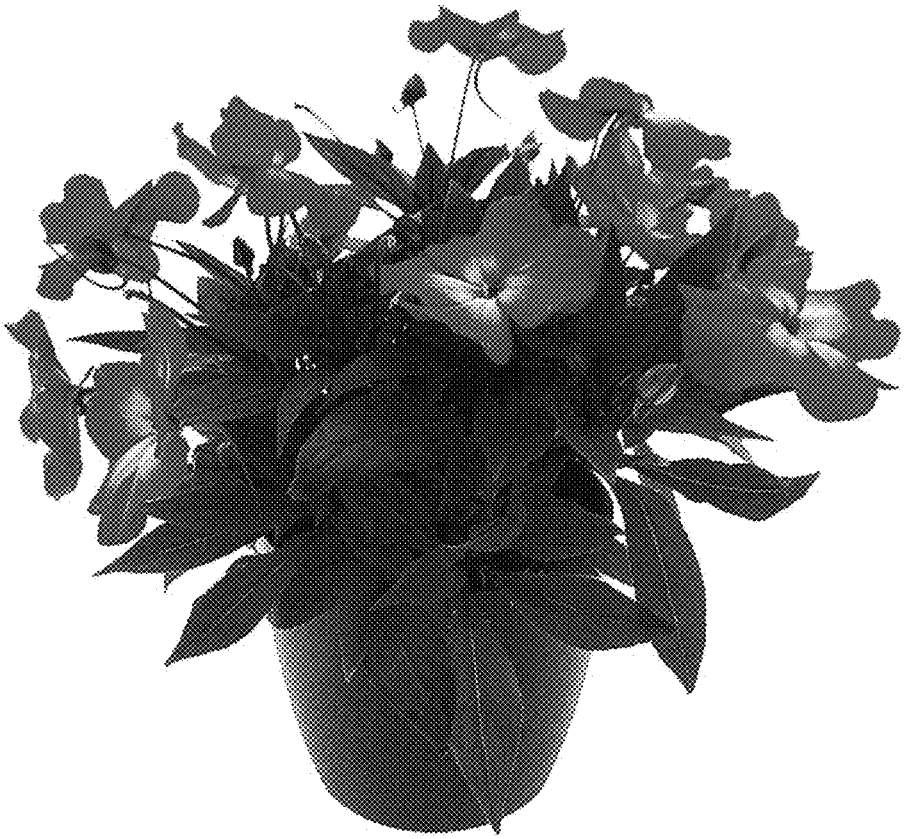

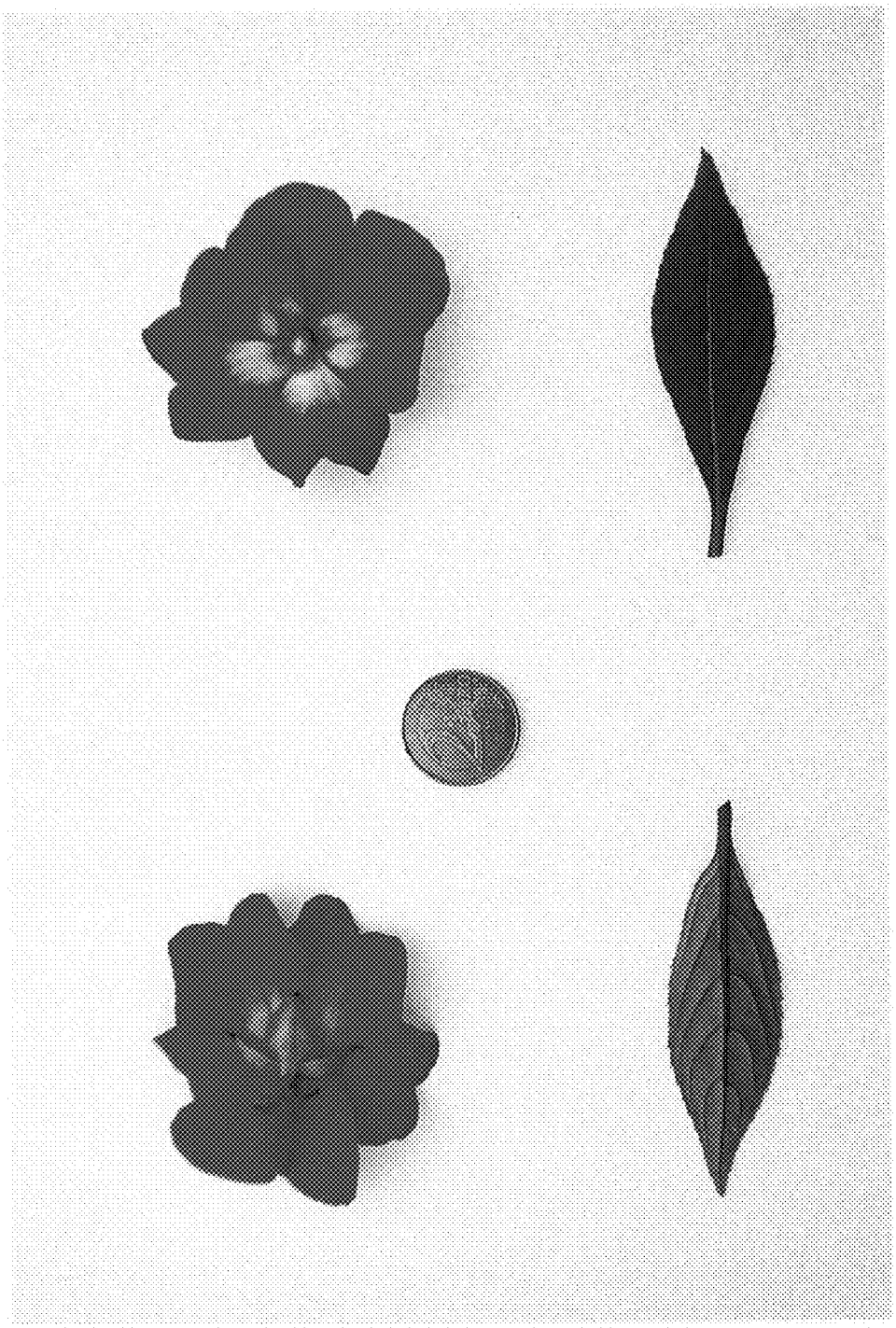

* * * * *